(12) United States Patent
Carter et al.

(10) Patent No.: US 7,932,090 B2
(45) Date of Patent: Apr. 26, 2011

(54) SAMPLE PROCESSING DEVICE POSITIONING APPARATUS AND METHODS

(75) Inventors: Chad J. Carter, Lake Elmo, MN (US); Christopher R. Kokaisel, St. Paul, MN (US); Kenneth B. Wood, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1184 days.

(21) Appl. No.: 10/911,875

(22) Filed: Aug. 5, 2004

(65) Prior Publication Data
US 2006/0029524 A1 Feb. 9, 2006

(51) Int. Cl.
G01N 35/10 (2006.01)
G01N 15/14 (2006.01)
B01L 3/00 (2006.01)

(52) U.S. Cl. .............. 436/47; 436/43; 436/50; 436/164; 436/165; 422/63; 422/65; 422/85.05; 356/244; 356/246; 435/288.5; 435/288.7; 435/287.2

(58) Field of Classification Search .................. None
See application file for complete search history.

(56) References Cited

U.S. PATENT DOCUMENTS

| | | | |
|---|---|---|---|
| 3,555,284 A | 1/1971 | Anderson | 250/218 |
| 3,795,451 A | 3/1974 | Mailen | 356/246 |
| 3,798,459 A | 3/1974 | Anderson et al. | 250/218 |
| 3,856,470 A | 12/1974 | Cullis et al. | |
| 3,873,217 A | 3/1975 | Anderson et al. | 356/246 |
| 3,938,958 A | 2/1976 | Lanier et al. | |
| 4,390,499 A | 6/1983 | Curtis et al. | |
| 4,632,908 A | 12/1986 | Schultz | |
| 4,673,657 A | 6/1987 | Christian | |
| 4,708,931 A | 11/1987 | Christian | |
| 4,806,316 A | 2/1989 | Johnson et al. | |
| 5,049,591 A | 9/1991 | Hayashi et al. | |
| 5,128,197 A | 7/1992 | Kobayashi et al. | |
| 5,135,786 A | 8/1992 | Hayashi et al. | |
| 5,139,832 A | 8/1992 | Hayashi et al. | |
| 5,145,935 A | 9/1992 | Hayashi | |
| 5,154,888 A | 10/1992 | Zander et al. | |
| 5,219,526 A | 6/1993 | Long | |

(Continued)

FOREIGN PATENT DOCUMENTS

EP 0 169 306 A2 1/1986

(Continued)

OTHER PUBLICATIONS

Product data sheet: "LabNEXT the Fine Art of Microarryaing, Product information for Xpand Membrane Kit" datasheet [online]. Lab Next LLC, Glenview, IL, No publication date [retrieved on May 26, 2004]. Retrieved from the Internet:<URL:http://labnext.com/MembraneKit.htm>; 2 pgs.

(Continued)

Primary Examiner — P. Kathryn Wright
(74) Attorney, Agent, or Firm — Nancy Lambert; Kevin Weber (57) ABSTRACT

Apparatus and methods for positioning the process chambers of microfluidic sample processing devices in the proper focal plane of a microplate reader are disclosed. The apparatus and methods may be adaptable to position the sample processing devices at different heights as may be necessary for processing in different microplate readers. A positioning device is used in connection with the sample processing device to locate the process chambers within the focal plane of the microplate reader.

15 Claims, 9 Drawing Sheets

U.S. PATENT DOCUMENTS

| | | | |
|---|---|---|---|
| 5,229,297 A | 7/1993 | Schnipelsky et al. | |
| 5,248,479 A | 9/1993 | Parsons et al. | |
| 5,254,479 A | 10/1993 | Chemelli | |
| 5,258,163 A | 11/1993 | Krause et al. | |
| 5,278,377 A | 1/1994 | Tsai | |
| 5,288,463 A | 2/1994 | Chemelli | |
| 5,310,523 A | 5/1994 | Smethers et al. | |
| 5,346,672 A | 9/1994 | Stapleton et al. | |
| 5,422,271 A | 6/1995 | Chen et al. | |
| 5,425,917 A | 6/1995 | Schmid | |
| 5,446,270 A | 8/1995 | Chamberlain et al. | |
| 5,453,246 A | 9/1995 | Nakayama et al. | |
| 5,460,780 A | 10/1995 | Devaney, Jr. et al. | |
| 5,461,134 A | 10/1995 | Leir et al. | |
| 5,516,581 A | 5/1996 | Kreckel et al. | |
| 5,529,708 A | 6/1996 | Palmgren et al. | |
| 5,587,128 A | 12/1996 | Wilding et al. | |
| 5,589,350 A * | 12/1996 | Bochner | 435/29 |
| 5,643,738 A | 7/1997 | Zanzucchi et al. | |
| 5,721,123 A | 2/1998 | Hayes et al. | |
| 5,726,026 A | 3/1998 | Wilding et al. | |
| 5,744,366 A | 4/1998 | Kricka et al. | |
| 5,800,785 A | 9/1998 | Bochner | |
| 5,804,141 A | 9/1998 | Chlanese | |
| 5,811,296 A | 9/1998 | Chemelli et al. | |
| 5,833,923 A | 11/1998 | McClintock et al. | |
| 5,863,502 A | 1/1999 | Southgate et al. | |
| 5,863,708 A | 1/1999 | Zanzucchi et al. | |
| 5,863,801 A | 1/1999 | Southgate et al. | |
| 5,876,675 A | 3/1999 | Kennedy | |
| 5,925,455 A | 7/1999 | Bruzzone et al. | |
| 6,004,512 A | 12/1999 | Titcomb et al. | 422/63 |
| 6,007,914 A | 12/1999 | Joseph et al. | |
| 6,013,513 A | 1/2000 | Reber et al. | |
| 6,030,581 A | 2/2000 | Virtanen | |
| 6,048,498 A | 4/2000 | Kennedy | 422/99 |
| 6,063,589 A | 5/2000 | Kellogg et al. | |
| 6,071,478 A | 6/2000 | Chow | 422/81 |
| 6,143,248 A | 11/2000 | Kellogg et al. | |
| 6,184,029 B1 | 2/2001 | Wilding et al. | |
| 6,191,852 B1 | 2/2001 | Paffhausen et al. | 356/244 |
| 6,319,469 B1 | 11/2001 | Mian et al. | |
| 6,399,025 B1 | 6/2002 | Chow | |
| 6,413,782 B1 | 7/2002 | Parce et al. | |
| 6,451,261 B1 | 9/2002 | Bodner et al. | |
| 6,508,988 B1 | 1/2003 | Van Dam et al. | |
| 6,514,750 B2 * | 2/2003 | Bordenkircher et al. | 435/286.2 |
| 6,565,752 B1 | 5/2003 | Baron et al. | |
| 6,623,860 B2 | 9/2003 | Hu et al. | |
| 6,627,159 B1 | 9/2003 | Bedingham et al. | |
| 6,642,953 B1 * | 11/2003 | Nieto Velasco et al. | 348/61 |
| 6,645,758 B1 | 11/2003 | Schnipelsky et al. | |
| 6,656,431 B2 | 12/2003 | Holl et al. | |
| 6,734,401 B2 | 5/2004 | Bedingham et al. | 219/388 |
| 6,750,039 B1 * | 6/2004 | Bargoot et al. | 435/34 |
| 6,770,441 B2 | 8/2004 | Dickinson et al. | |
| 6,814,935 B2 | 11/2004 | Harms et al. | |
| 6,830,729 B1 | 12/2004 | Holl et al. | |
| 7,022,290 B2 | 4/2006 | Gural et al. | |
| 7,026,168 B2 | 4/2006 | Bedingham et al. | |
| 7,048,893 B2 | 5/2006 | Bellon | |
| 7,056,475 B2 | 6/2006 | Lum et al. | |
| 7,105,354 B1 | 9/2006 | Shimoide et al. | |
| 7,135,147 B2 | 11/2006 | Cox et al. | |
| 7,198,759 B2 | 4/2007 | Bryning et al. | |
| 7,201,881 B2 | 4/2007 | Cox et al. | |
| 7,214,348 B2 | 5/2007 | Desmond et al. | |
| 7,445,752 B2 | 11/2008 | Harms et al. | |
| 2002/0031836 A1 | 3/2002 | Feldstein | |
| 2002/0048533 A1 * | 4/2002 | Harms et al. | 422/99 |
| 2002/0064885 A1 | 5/2002 | Bedingham et al. | |
| 2003/0008383 A1 * | 1/2003 | Bordenkircher et al. | 435/286.2 |
| 2003/0148537 A1 | 8/2003 | Bellon | |
| 2003/0152994 A1 | 8/2003 | Woudenberg et al. | |
| 2003/0214650 A1 | 11/2003 | Dietz et al. | 356/246 |
| 2003/0228242 A1 | 12/2003 | Feygin | |
| 2003/0228701 A1 | 12/2003 | Wong et al. | |
| 2004/0018117 A1 | 1/2004 | Desmond et al. | |
| 2004/0023371 A1 | 2/2004 | Fawcett | |
| 2004/0071605 A1 | 4/2004 | Coonan et al. | |
| 2004/0121471 A1 | 6/2004 | Dufresne et al. | |
| 2005/0148091 A1 | 7/2005 | Kitaguchi et al. | |
| 2005/0232818 A1 | 10/2005 | Sandell et al. | |
| 2006/0188396 A1 | 8/2006 | Bedingham et al. | |
| 2007/0014695 A1 | 1/2007 | Yue et al. | |
| 2008/0287307 A1 * | 11/2008 | Adrien et al. | 506/7 |

FOREIGN PATENT DOCUMENTS

| | | |
|---|---|---|
| EP | 0 402 994 A2 | 12/1990 |
| EP | 0 693 560 A2 | 1/1996 |
| EP | 1 358 939 A2 | 11/2003 |
| WO | WO 94/26414 | 11/1994 |
| WO | WO 94/29400 | 12/1994 |
| WO | WO 95/18676 | 7/1995 |
| WO | WO 96/15576 | 5/1996 |
| WO | WO 96/34028 | 10/1996 |
| WO | WO 96/34029 | 10/1996 |
| WO | WO 96/35458 | 11/1996 |
| WO | WO 96/41864 | 12/1996 |
| WO | WO 97/21090 | 6/1997 |
| WO | WO 98/07019 | 2/1998 |
| WO | WO 98/49340 | 11/1998 |
| WO | WO 99/09394 | 2/1999 |
| WO | WO99/28436 * | 6/1999 |
| WO | WO 99/44740 | 9/1999 |
| WO | WO 99/55827 | 11/1999 |
| WO | WO 99/58245 | 11/1999 |
| WO | WO 99/67639 | 12/1999 |
| WO | WO 00/05582 | 2/2000 |
| WO | WO 00/17624 | 3/2000 |
| WO | WO 00/40750 | 7/2000 |
| WO | WO 00/50172 | 8/2000 |
| WO | WO 00/50642 | 8/2000 |
| WO | WO 00/68336 | 11/2000 |
| WO | WO 00/69560 | 11/2000 |
| WO | WO 00/78455 | 12/2000 |
| WO | WO 00/79285 | 12/2000 |
| WO | WO 01/07892 | 2/2001 |
| WO | WO 02/01180 | 1/2002 |
| WO | WO 02/01181 | 1/2002 |
| WO | WO 2004/011132 | 2/2004 |
| WO | WO 2004/011148 | 2/2004 |
| WO | WO 2004/011149 | 2/2004 |
| WO | WO 2004/011365 | 2/2004 |
| WO | WO 2004/011592 | 2/2004 |

OTHER PUBLICATIONS

Unger, M. et al.; "Monolithic Microfabricated Valves and Pumps by Multilayer Soft Lithography"; Science; vol. 288, Apr. 7, 2000; pp. 113-116 XP-002192277.

Handbook of Pressure Sensitive Adhesive Technology; Second Edition; Donatas Satas; Van Nostrand Reinhold, New York, NY 1989 pp. copyright, 172, Fig. 8-16 on 173.

Handbook of Pressure Sensitive Adhesive Technology; Second Edition; Donatas Satas; Van Nostrand Reinhold, New York, NY 1989 pp. copyright, 508-517.

Test Methods for Pressure Sensitive Adhesive Tapes; 13th Edition; Pressure Sensitive Tape Council; 2000; pp. table of contents and pp. 23-34.

Test Methods for Pressure Sensitive Tapes; 7th Edition; Pressure Sensitive Tape Council; 1976; pp. table of contents and p. 6.

Draft Product Information Sheet for Microplates—Height Dimensions; Society for Biomolecular Screening dated May 9, 2002 (10 pgs.).

Draft Product Information Sheet for Microplates—Footprint Dimensions; Society for Biomolecular Screening dated Jan. 17, 2002 (8 pgs.).

* cited by examiner

SAMPLE PROCESSING DEVICE POSITIONING APPARATUS AND METHODS

The present invention is directed to methods and apparatus for positioning sample processing devices for optical interrogation. More specifically, the invention is directed to apparatus for placing a sample processing device at a height chosen so as to match the focal plane of a microplate reader. Preferably, the sample processing device is positioned such that all the process chambers are uniformly aligned in this plane.

Sample processing devices may be used for performing biological or chemical reactions and assays with small volumes of reagent and sample. Some microfluidic devices are described in U.S. Pat. No. 6,627,159 B1 (Bedingham et al.) and U.S. Patent Application Publication Nos. U.S. 2002/0048533 A1 (Harms et al.) and U.S. 2002/0064885 (Bedingham et al.). The microfluidic devices described in those documents may include laminated structures of a first layer with features such as process chambers and conduits embossed therein, and a second layer, which is typically flat, and forms the backside of the device. Typically, the conduits are used to deliver liquid samples to the process chambers. Reactions are typically carried out in the process chambers. Most often, the progress of the reaction is monitored in these same process chambers via optical techniques such as fluorescence, absorbance, etc. Accordingly, the first layer is typically constructed of transmissive material so that the reaction can be optically interrogated through this layer. The microfluidic devices may be provided with or without carriers as described in the above-identified documents.

The process chambers are often present in arrays, such as in groups of 96 or 384 per device. Such arrays typically correspond to the standard formats in which conventional microtiter plates are available. Alternatively, the process chambers can be present in groupings and/or spacings that are chosen for specific applications or needs.

Microfluidic devices that include conduits and process chambers may be distinguished from conventional microtiter plates by virtue of their low profile. That is, the fluidic body of the microfluidic device is typically very thin, often one millimeter thick or less. As a result, the process chambers in such sample processing devices are typically less than one millimeter tall. That is, the process chamber volume extends less than one millimeter in the z-axis dimension (perpendicular to the flat plane of the sample processing device).

This is in sharp contrast to conventional microtiter plates, for which the z-axis depths of the sample wells are much greater, typically in the range of several millimeters. Thus, for a process chamber on a microfluidic sample processing device, the z-axis distance over which interrogatable liquid sample is present can be extremely small in comparison to that of conventional microtiter plates.

The fact that process chambers in microfluidic sample processing devices have a very small z-axis dimension presents challenges if the microfluidic sample processing device is to be interrogated optically. Specifically, in attempting to interrogate the device with a scanner or microplate reader, it may be difficult to bring the array of process chambers into proper coincidence with the "focal plane" of the microplate reader (that is, the z-axis location, relative to the flat plane established by the floor of the chamber into which the microtiter plate or microfluidic sample processing device is to be inserted, at which the microplate reader is capable of providing the strongest optical signal). Microplate readers typically provide a floor or other surface upon which a device such as a microtiter plate is placed in order to be optically interrogated. Often, the focal plane of the microplate reader may be several millimeters above the floor of the sample compartment (or other surface on which the sample processing device rests). This presents no difficulty for such devices as standard microtiter plates. However, because of their reduced thickness, the process chambers of the microfluidic sample processing device would rest close to the floor of the sample compartment, often below the focal plane of the microplate reader.

An additional challenge in the use of some microfluidic sample processing devices is that even if the sample processing devices can be placed nominally in coincidence with the focal plane, all of the process chambers may not be aligned properly because the sample processing device itself may possess curl or warpage. In contrast, conventional microtiter microplates, by virtue of being thick, inflexible bodies with sample wells that extend several millimeters along the z-axis, are inherently capable of being positioned such that at least some portion of the liquid sample in each of the individual wells lies within the optimum focal plane of the microplate reader.

SUMMARY OF THE INVENTION

The present invention provides apparatus and methods for positioning the process chambers of microfluidic sample processing devices in the proper focal plane of a microplate reader. The apparatus and methods may be adaptable to position the sample processing devices at different heights as may be necessary for processing in different microplate readers. Furthermore, because of the small sample volume and resulting low signal strength that may be encountered with process chambers in microfluidic sample processing devices, it may be preferred that the materials used in the various components of the invention do not significantly adversely impact the signal that may be obtained from the process chambers upon optical interrogation. It may further be preferred that the positioning be accomplished without the application of external force on the sample processing device (such as, e.g., a microplaten) that could interfere with the interrogation process.

The present invention involves use of a positioning device in connection with the sample processing device to locate the process chambers within the focal plane of the microplate reader. The positioning device preferably rests on the floor of the sample compartment of a microplate reader, and is designed with a z-axis height so as to place the process chambers in the proper focal plane of the given microplate reader. In some embodiments, the microfluidic sample processing device may preferably be designed so that the weight of the sample processing device itself, in combination with the support provided by the positioning device, are such that the sample processing device can be held sufficiently flat so that all the process chambers reside uniformly in the focal plane. To this end, it may be preferred that the positioning device provide support underneath the entire area occupied by the process chambers, as opposed to providing support only around the perimeter of the sample processing device.

A wide variety of sample processing devices may be used in connection with the apparatus and methods of the present invention, although some suitable sample processing devices may include those described in, e.g., U.S. Pat. No. 6,627,159 B1 (Bedingham et al.) and U.S. Patent Application Publication Nos. U.S. 2002/0048533 A1 (Harms et al.) and U.S. 2002/0064885 (Bedingham et al.). The phrase "sample processing device" may be used in the above-identified documents to identify a fluidic device (including process chambers, conduits, and other fluid transfer features) that may be attached to a separate carrier. As used in connection with the present invention, however, a "sample processing device" encompasses both a fluidic device (containing process chambers, conduits and other fluid transfer features) alone and the combination of a carrier and a fluidic device. In other words, in some embodiments, the fluidic device may be used alone in connection with a positioning device according to the present invention, and in other embodiments the sample processing device used in connection with the positioning device may include a fluidic device and associated carrier.

Other potentially useful features may optionally be provided in connection with the present invention. Mating features (including, but not limited to, posts and openings) may be designed not only for registration, but may also serve to snap the sample processing device and positioning device together if needed in order to apply sufficient force to hold the sample processing device flat. In other words, the sample processing device may be held flat against the positioning device not simply by the weight of the sample processing device itself, but by the forces generated by snap-together functionality of the assembly, without requiring the presence of an external force to be applied during the optical interrogation of the microfluidic sample processing device. Alternatively, forces may be provided to retain the sample processing device on the positioning device using clamps, adhesives, magnetic attraction, etc. It may, however, be preferred that any such features, structures, etc. be contained within the assembly of the sample processing device and positioning device (i.e., that no external forces be required).

It may be preferred that the positioning device possess one or more corners suitable for positioning the sample processing device accurately in the xy plane of the microplate reader. For example, such positioning can often be achieved by simply placing the corner of the positioning device flush against a corner of the microplate reader sample compartment floor (as is frequently done with microtiter microplates).

The sample processing device and the positioning device may also include features that assist in the temporary separation and/or handling of the two devices. Such features may include, e.g., scallops, notches, grooves, etc., which provide for easy gripping.

The sample processing device and the positioning device may also preferably include features that enable stacking. It may be preferred that the sample processing devices and positioning devices have features such that sets of complete assemblies (sample processing device and positioning device) can be stacked as desired. It may also be preferred that the positioning devices have features such that sets of positioning devices can be stacked (which may be useful for shipping and storage).

The sample processing device and the positioning device are preferably supplied as an assembly. In some circumstances, it may be necessary that the two devices are temporarily separated for a particular processing step (such as sealing of the sample processing device) prior to optical interrogation. However, the two devices are typically required to be rejoined into an assembly prior to optical interrogation. In an alternative embodiment, the two devices may be provided as a kit. In this embodiment, it is again typically required that the two devices are joined into an assembly prior to optical interrogation.

In some embodiments, the sample processing device and positioning device may be connected together by one or more hinges such that the two components are attached, but access is provided to the surface of the sample processing device facing the positioning device when the components are rotated into a closed position about the hinge or hinges. That access to the sample processing device may be helpful for loading sample materials, staking fluid delivery channels, thermal processing of the sample processing device, etc.

The sample processing devices (or portions thereof) and the positioning devices may preferably be constructed of molded plastic pieces, e.g., by injection molding. Alternatively, the sample processing devices (or portions thereof) and/or positioning devices may be machined out of solid blocks (e.g., plastic, metal, etc.) to form the desired structures. It may be preferred that that the materials used do not significantly adversely affect the optical signal. For example it may be advantageous to use nonfluorescent materials if the process chambers are to be interrogated by optical fluorescence.

In one method of use, a microfluidic sample processing device may be loaded with sample material and/or processed (i.e. incubated) before attaching the sample processing device to the positioning device for optical interrogation. When the process chambers of the sample processing device are to be interrogated, the sample processing device is mated with the positioning device. The completed assembly can then be placed in the microplate reader such that the array of process chambers is positioned in the focal plane of the microplate reader. This placement may be performed manually, in which case proper lateral (xy) positioning of the sample processing device may be achieved by, e.g., butting a corner of the assembly into the corner of the microplate reader floor so as to align the assembly properly in the microplate reader. The process chambers are then interrogated, after which the assembly can be removed.

In an alternative embodiment, the assembly may be brought into place in the sample compartment of the microplate reader using robotic handling. For example, the assembly can be placed in the loading tray of a microplate reader, which then moves the assembly into position inside the sample compartment of the microplate reader for interrogation. For purposes of the present invention, the "floor" of the sample compartment in embodiments using a loading tray is the surface of the loading tray that supports the positioning device and the sample processing device.

While the primary purpose of the positioning device is to facilitate optical interrogation of the sample processing device in a microplate reader, the sample processing device can also be placed on the positioning device during other processing before or after the optical interrogation. For example, if the sample processing device is to be held in an incubator or oven, placed in a refrigerator, etc., this can be done with the sample processing device already positioned upon the positioning device.

In one aspect, the present invention provides a method of positioning a sample processing device within a microplate reader having a sample compartment with a floor and a focal plane spaced from the floor of the sample compartment. The method includes providing a sample processing device having at least one process array, wherein the at least one process array includes a main conduit and a plurality of process chambers located along the main conduit, and wherein the sample processing device includes a first major surface with edges at a periphery of the first major surface;

locating a positioning device proximate the first major surface of the sample processing device; and locating the sample processing device and the positioning device in the sample compartment of the microplate reader, wherein the positioning device is located between the first major surface of the sample processing device and the floor of the sample compartment.

In another aspect, the present invention provides a method of positioning a sample processing device within a microplate reader having a sample compartment with a floor on which a sample processing device rests during reading. The method includes providing a sample processing device having at least one process array, wherein the at least one process array includes a main conduit and a plurality of process chambers located along the main conduit, and wherein the sample processing device includes a first major surface with edges at a periphery of the first major surface; suspending the sample processing device within a positioning device, wherein the sample processing device is retained within the positioning device along two or more of the edges of the sample processing device; placing the sample processing device and the positioning device in the sample compartment of the microplate reader, wherein the positioning device positions the first major surface of the sample processing device at a selected distance from the floor of the sample compartment.

In another aspect, the present invention provides a sample processing kit that includes a sample processing device having at least one process array, wherein the at least one process array includes a main conduit and a plurality of process chambers located along the main conduit, wherein the main conduit is open along its length, and wherein the sample processing device includes a first major surface with edges at a periphery of the first major surface; a positioning device with two major surfaces arranged generally parallel to each other, wherein the two major surfaces includes a support surface and a base surface opposite the support surface, wherein the support surface is substantially coextensive with an area of the first major surface occupied by the plurality of process chambers of the at least one process array; and first alignment features on the support surface of the positioning device and complementary second alignment features on the sample processing device, wherein the first alignment features and the second alignment features operably connect to align the sample processing device on the support surface of the positioning device; wherein the sample processing device is not fixedly attached to the positioning device.

In another aspect, the present invention provides a sample processing kit that includes a sample processing device having at least one process array, wherein the at least one process array includes a main conduit and a plurality of process chambers located along the main conduit, wherein the main conduit is open along its length, and wherein the sample processing device includes a first major surface with edges at a periphery of the first major surface; and a positioning device with two or more opposing channels adapted to suspend the sample processing device within the positioning device; wherein the sample processing device is not fixedly attached to the positioning device.

These and other features and advantages that may be provided in connection with the present invention may be described in connection with various exemplary embodiments of the invention below.

DETAILED DESCRIPTION OF EXEMPLARY EMBODIMENTS OF THE INVENTION

As discussed above, the present invention provides methods and apparatus for positioning sample processing devices within microplate readers. In the following descriptions of exemplary embodiments of the invention, reference may be made to the accompanying figures which form a part hereof, and in which are shown, by way of illustration, specific exemplary embodiments in which the invention may be practiced. It is to be understood that other embodiments may be utilized and structural changes may be made without departing from the scope of the present invention.

The present invention provides methods and apparatus adapted to position sample processing devices relative to the focal plane of a microplate reader such that the process chambers in the sample processing device are located within the focal plane. By so doing, the accuracy with which results can be obtained using shallow well sample processing devices may be improved.

Although terms such as "above," "below," "floor," etc. may be used in connection with the present invention, it should be understood that those terms are used in their relative sense only. For example, when used in connection with the devices of the present invention, "floor" is used only to signify a surface against which the positioning device rests during interrogation. Although the floor may often be found at the bottom of, e.g., a sample compartment (when considering the direction of gravitational force), the use of the term floor is not meant to require that the floor actually be at the bottom of the sample compartment.

In actual use, a surface described as a "floor" may be found in any orientation or location and should not be considered as limiting the methods and apparatus to any particular orientation or location. For example, the floor of a sample compartment may actually be located above (with respect to gravitational forces) a sample processing device and positioning device when those two components are loaded into the sample compartment.

Figure 1:
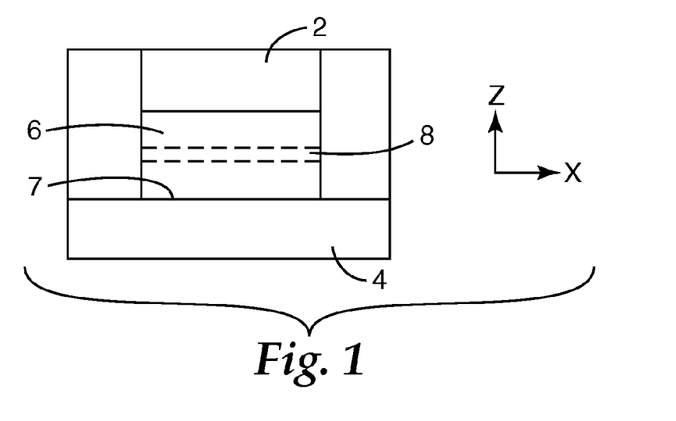
FIG. 1 is a schematic diagram of one exemplary microplate reader with which the methods and apparatus of the present invention may be used.
Figure 1A:
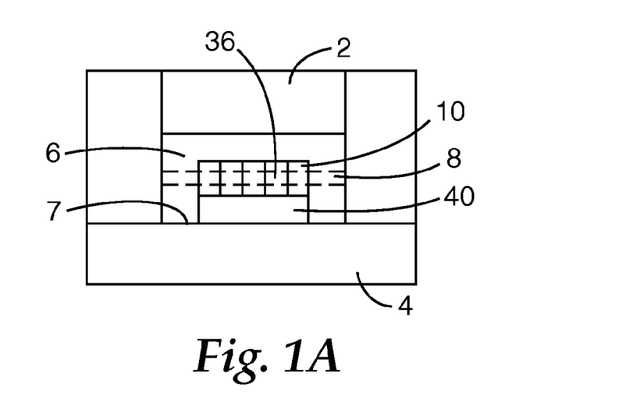
FIG. 1A is a schematic diagram of one exemplary microplate reader with a sample processing device having process chambers located in the focal plane of the reader when a positioning device is located between the sample processing device and the floor of the sample compartment.
Figure 1B:
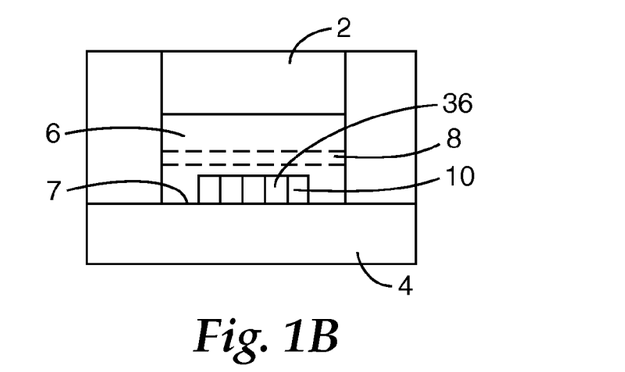
FIG. 1B is a schematic diagram of one exemplary microplate reader with a sample processing device having process chambers that are not located in the focal plane of the reader when a positioning device is not located between the sample processing device and the floor of the sample compartment.

A schematic diagram of one exemplary microplate reader is provided in FIG. 1 in which the optical reader 2 is located above a sample compartment 6 formed in the lower portion 4 of the microplate reader. The sample compartment includes a floor 7 on which a sample processing device rests during the reading process. Typically, the optical components of the optical reader 2 will define a focal plane 8 within the sample compartment 6 that is located at some distance from the floor 7. The focal plane 8 defines a location within which sample material may preferably be located for reading by the optical reader 2. Although described as a "plane," it should be understood that the optical plane 8 may have some thickness in the z-axis depending on the optics used in the optical reader 2. FIG. 1A depicts the microplate reader of FIG. 1 with a sample processing device 10 with process chambers 36 in the sample compartment 6 and a positioning device 40 located between the sample processing device 10 and the floor 7 of the sample compartment 6. FIG. 1B depicts the sample processing device 10 located on the floor 7 of the sample compartment 6 (with no positioning device located between the sample processing device 10 and the floor 7). The process chambers 36 are located in the focal plane 8 in FIG. 1A and the process chambers 36 are not located in the focal plane 8 in FIG. 1B.

Although the microplate reader of FIG. 1 is depicted as a top-reading system, i.e., one in which the optical reader 2 is located above the floor 7 of the sample compartment 6, it should be understood that on at least some embodiments, the present invention may also be used in connection with microplate readers that read from the opposite direction, i.e., below the sample processing device as loaded in the sample compartment. In such a system, the optical reader may direct optical energy towards a sample processing device located within the sample compartment 6 from the direction of the floor 7. In many instances, such a system may require that the optical interrogation energy pass through the positioning device before reaching the sample processing device. In addition, the surfaces of the process chambers of the sample processing device facing the optical reader will preferably be transmissive to the optical interrogation energy.

Figure 2:
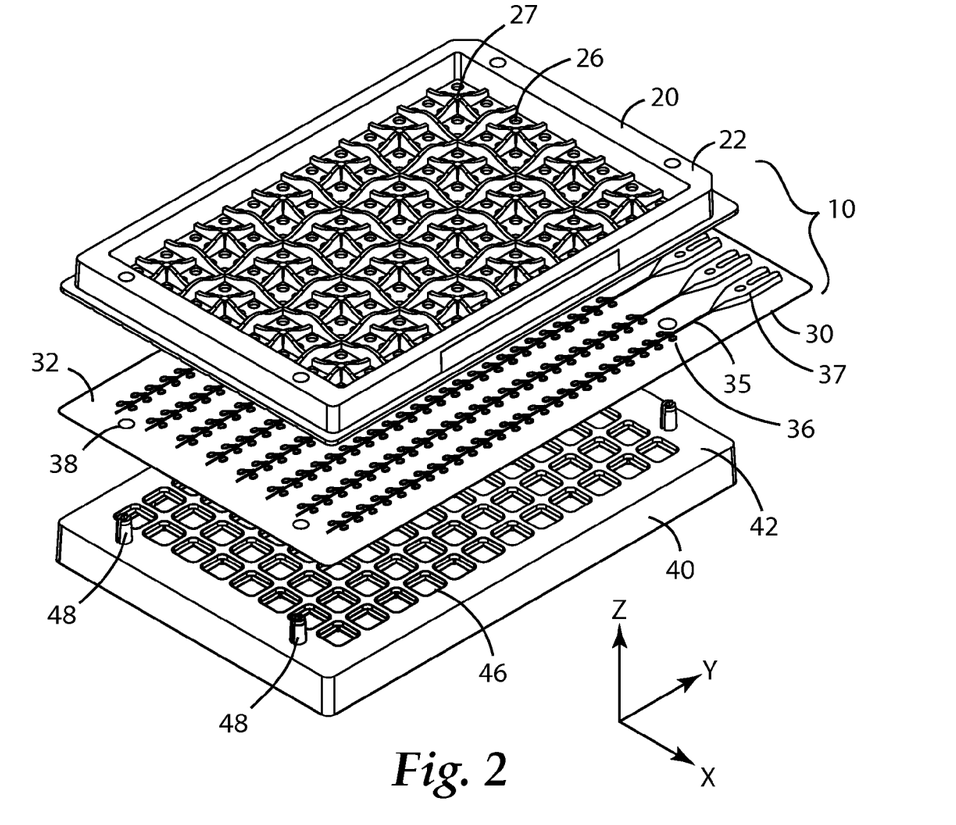
FIG. 2 is an exploded perspective view of one exemplary embodiment of a sample processing device and positioning device according to the present invention.
Figure 3:
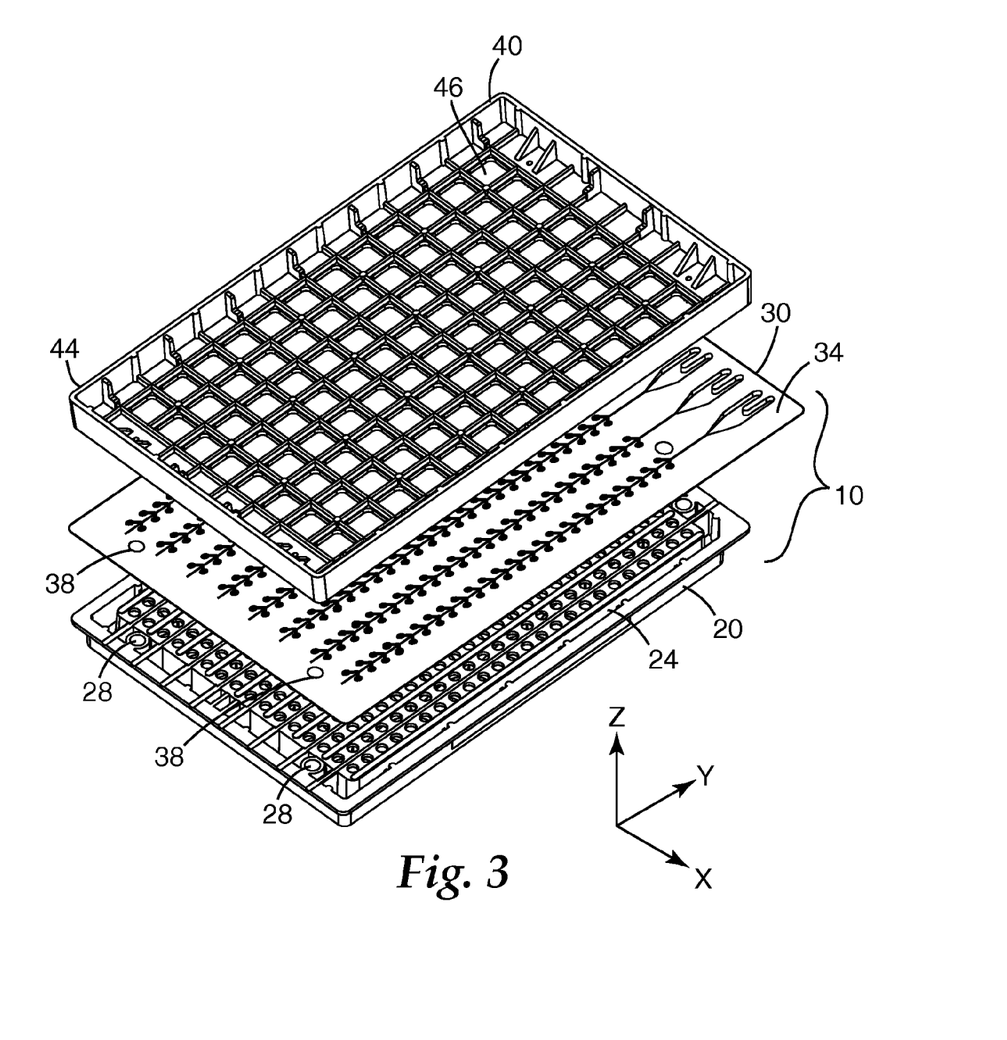
FIG. 3 is an exploded perspective view of the sample processing device and positioning device of FIG. 2 taken from the opposite side of the positioning device.

FIGS. 2 & 3 depict opposite perspective views of an exploded system of the present invention. The system includes a sample processing device 10 that includes both a carrier 20 and a fluidic device 30 that will typically be supplied attached to the carrier 20. In FIGS. 2 & 3, however, the assembly is depicted in exploded form to assist with description of the various components in this exemplary embodiment of the invention.

The carrier 20 preferably includes two major surfaces 22 (see FIG. 2) and 24 (see FIG. 3). Surface 22 faces away from the fluidic device 30 and surface 24 faces towards the fluidic device 30. The carrier 20 also preferably includes voids 26 formed therethrough that are preferably aligned with process chambers 36 in the fluidic device 30. The voids 26 preferably allow for the transmission of light (ultraviolet, visible, infrared, and combinations thereof) into and/or out of the process chambers 36. As seen in FIG. 2, the carrier 20 may also preferably include structures 27 designed to transfer compressive forces to the fluidic device 30 as discussed in a number of the documents identified herein.

The fluidic device 30 preferably includes a major surface 32 (see FIG. 2) that faces the carrier 20 and an opposing major surface 34 (see FIG. 3) that faces away from the carrier 20. The fluidic device 30 of the sample processing device 10 also preferably includes at least one process array, where each process array preferably includes a main conduit 35 with process chambers 36 distributed along the main conduit 35. Each process array may preferably include a loading structure in the form of, e.g., a reservoir 37 that may be used to deliver fluids, sample materials, etc. to the process chambers 36 through the main conduit 35.

Details of some potentially preferred constructions for the carrier 20 and fluidic device 30 of the sample processing device 10 may be found in the documents identified above. For example, it may be preferred that the fluidic device 30 be constructed using a formed polymeric material laminated to a metallic foil layer such that deformation of the metallic foil may be used to close the main conduit and isolate the various process chambers from each other. An adhesive may be provided within the main conduit to assist in sealing of the main conduit and isolation of the process chambers.

The embodiment depicted in FIGS. 2 & 3 also includes a positioning device 40 that is preferably selected to position the process chambers 36 of the sample processing device 10 within the focal plane of a microplate reader such as, e.g., the microplate reader depicted in FIG. 1. The positioning device 40 preferably includes a support surface 42 and a base 44 opposite the support surface 42. When placed in the sample compartment of an microplate reader, the base 44 preferably contacts the floor of the sample compartment. The support surface 42 is the surface on which a sample processing device 10 is located.

It may be preferred that the support surface 42 be substantially coextensive with an area of the major surface 34 of the sample processing device 10 that is occupied by the process chambers 36 such that the height of the process chambers 36 within a sample compartment of an microplate reader can be controlled using the positioning device 40. Although the support surface 42 is described as being coextensive with the area occupied by the process chambers 36, it should be understood that "coextensive" (as used herein) means that the support surface 42 is at least as large as the area occupied by the process chambers 36, but may be larger. In other embodiments, the support surface 42 of the positioning device 40 may be smaller than the area occupied by the process chambers 36. Also, in some embodiments (such as that depicted in FIGS. 2 & 3), portions of the sample processing device 10 may not be supported by the positioning device 40. As depicted, the portion of the fluidic device 30 containing reservoirs 37 is located outside of the support surface 42 of the positioning device 40.

Because the positioning device 40 has a thickness in the z-axis (between the support surface 42 and the base 44), the process chambers 36 of the sample processing device 10 are preferably located within an optical plane of a microplate reader. The thickness of the positioning device 40 used in connection with a particular sample processing device and/or microplate reader may be selected to locate the process chambers in the optical plane. For example, since the location of the optical plane may vary between different microplate readers, the exact location of the process chambers in a particular sample processing device may vary. The positioning device will be supplied with a thickness appropriate to place the sample processing device in the focal plane of the given microplate reader. In another technique, a sample positioning device may be provided with one or more shims that may be used to increase the thickness of the positioning device until a selected thickness is obtained that places the process chambers within the focal plane of the microplate reader.

An optional feature depicted in connection with positioning device 40 are voids 46 located in the support surface 42. It may be preferred that the voids 46 extend through the positioning device 40 such that objects on the support surface 42 can be seen by a viewer on the side of the base 44 of the positioning device 40. It may be preferred in some embodiments that the voids 46 be aligned with the process chambers 36 of the sample processing device 10.

The positioning device 40 may include any number of voids 46, including as few as one void. For example, in some embodiments, the positioning device may include one large void such that the positioning device provides a frame or skirt above which the sample processing device 10 is suspended. Such an embodiment may function best when the process chambers are located in a relatively rigid assembly such that the location of the process chambers is consistent over the surface of the sample processing device. In some instances, the sample processing device itself may be constructed with a frame or skirt integral thereto (e.g., molded as a one-piece integral unit or other wise fixedly attached) such that a separate positioning device need not be provided to locate the process chambers in the focal plane of the microplate reader.

It may be preferred that the sample processing devices and positioning devices of the present invention include alignment features such that the sample processing devices can be aligned with the positioning device. This may be useful where, for example, the sample compartment of the microplate reader in which the assembly is to be located includes alignment features designed to align the process chambers of a sample processing device with the microplate reader. In such a system, the positioning device 40 may be accurately located within the sample compartment and the process chambers 36 of the sample processing device 10 may then also be accurately located using alignment features on the positioning device 10.

The alignment features may take a variety of forms. In the embodiment depicted in FIGS. 2 & 3, the alignment features include posts 48 protruding from the support surface 42 of the positioning device 40. The sample processing device 10 preferably includes complementary alignment features in the form of openings 38 in the fluidic device 30 and openings 28 in the carrier 20 (see FIG. 2). The openings 28/38 and posts 48 may preferably be keyed or arranged in a manner that allows mating of the sample processing device 10 and positioning device 40 in only one orientation to ensure proper alignment of the components. It should be understood that among the many possible variations in alignment features, the opposite arrangement may also be contemplated, i.e., the sample processing device 10 may include posts and the positioning device 40 may include openings sized to receive the posts.

Although not shown, the positioning device 40 may include sleeves opening onto the base surface 44 such that posts protruding from the floor of the sample compartment may be received in the sleeves to align the positioning device 40 in the sample compartment. Because the alignment features described above between the sample processing device 10 and the positioning device 40 accurately align those components, the process chambers 36 may preferably be provided in selected locations in the sample compartment.

In addition to the alignment structures described above, in some instances the structures used to retain the sample processing devices on the positioning devices may also function to align the sample processing devices on the positioning devices. Such dual-function structures may include, e.g., the clamps, locking tabs, hinges, etc. described herein.

Also, although not shown, one corner of each component of the assembly, i.e., one corner of each of the sample processing device 10 and the positioning device 40 may be provided with a diagonal flat as is used in conventional titer microplates to assist in proper orientation of the assembly within a sample compartment of an microplate reader.

The sample processing device 10 and the positioning device 40 may also preferably include means for retaining the sample processing device 10 proximate the support surface 42 of the positioning device 40. In some instances, it may be desirable to provide sufficient force to flatten the sample processing device if it has a curvature that may cause some of the process chambers to be located outside of the focal plane. That force may, in some instances, be provided by the weight of the sample processing device itself (e.g., the carrier 20 may have sufficient mass such that the fluidic device is flattened against the support surface 42 of the positioning device).

A variety of different techniques may be used to retain the sample processing device 10 on the positioning device 40. One technique may include, e.g., sizing the openings 28/38 and posts 48 such that a friction fit is obtained that retains the sample processing device 10 on the positioning device 40. Other potential constructions may include, e.g., providing a shoulder or other feature on the posts 48 that effectively engages a complementary feature in the openings 28/38 of the sample processing device to retain the sample processing device 10 on the positioning device 40. Such a construction may be referred to as a "snap-fit" and the features that engage each other may take many different forms that are known to those of skill in the art.

Figure 4:
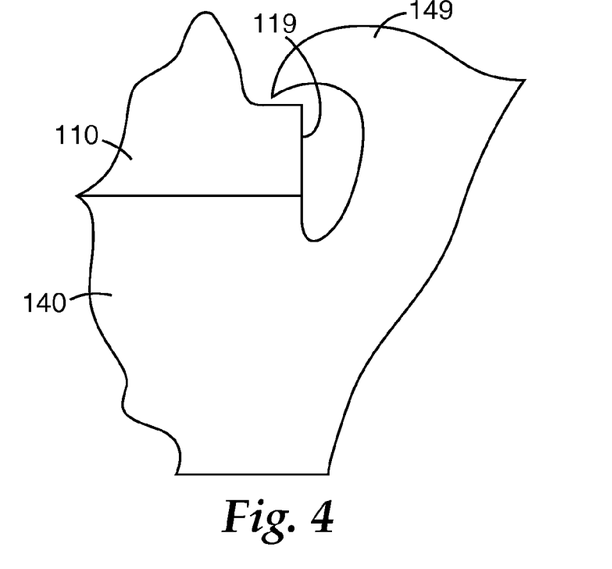
FIG. 4 is a view of an exemplary clamp retaining an edge of a sample processing device against a positioning device in accordance with the present invention.

Another technique of retaining the sample processing device on the positioning device is to provide a retaining assembly. As depicted in FIG. 4, one embodiment of a retaining assembly includes a clamp 149 adapted to retain the sample processing device 10 on the positioning device 140. The depicted clamp 149 may preferably be formed as an integral part of one of the components. In the embodiment of FIG. 4, the clamp 149 is an integral part of the positioning device 140. Alternatively, one or more clamps that are separate and independent of the sample processing device 110 and the positioning device 140 may be used to retain the sample processing device 110 on the positioning device. Separate clamps may provide their clamping force by any suitable technique, e.g., magnetic, springs, resilient members, screw clamps, etc.

The clamp 149 may preferably be biased into the position seen in FIG. 4, where the clamp overlaps the edge 119 of the sample processing device 110 to retain the sample processing device 110 on the positioning device 140. The biasing force may be provided by resiliency in the materials used to form the clamp 149. Alternatively, separate resilient members such as springs, elastomeric bands, etc. may be used to provide a biasing force to the clamp. In still other alternatives, magnetic attraction may provide the biasing force.

Figure 5:
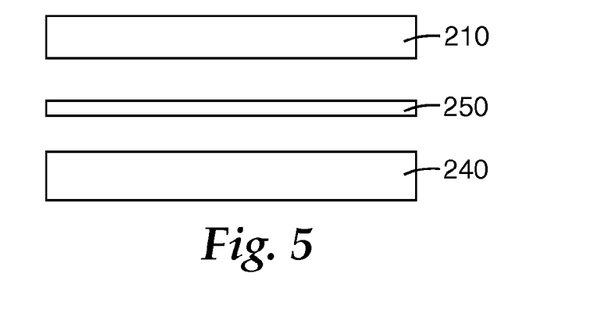
FIG. 5 is a perspective view of a sample processing device and positioning device with adhesive for attaching the sample processing device to the positioning device.

FIG. 5 depicts another technique for retaining the sample processing device 210 on the positioning device 240. The technique includes the use of adhesive 250 between the sample processing device 210 and the positioning device 240. Although the adhesive is depicted as a solid layer, it should be understood that the adhesive may be provided in any suitable form, e.g., solid layer, patterned layer including voids, spots, strips, etc. Furthermore, the adhesive may be provided on the sample processing device 210, the positioning device 240, both components, as a separate article interposed between the sample processing device 210 and the positioning device 240, and any combination thereof.

The adhesive may be any suitable adhesive, e.g., pressure sensitive, curable, hot melt, etc. In some embodiments it may be preferred that the adhesive used be releasable, e.g., have a low tack similar to, e.g., POST-IT note adhesive. In other embodiments, it may be desirable to use stretch-releasable adhesives with or without tabs (some examples of potentially suitable stretch releasable adhesives may be described in, e.g., U.S. Pat. No. 5,516,581 to Kreckel et al.)

Figure 6:
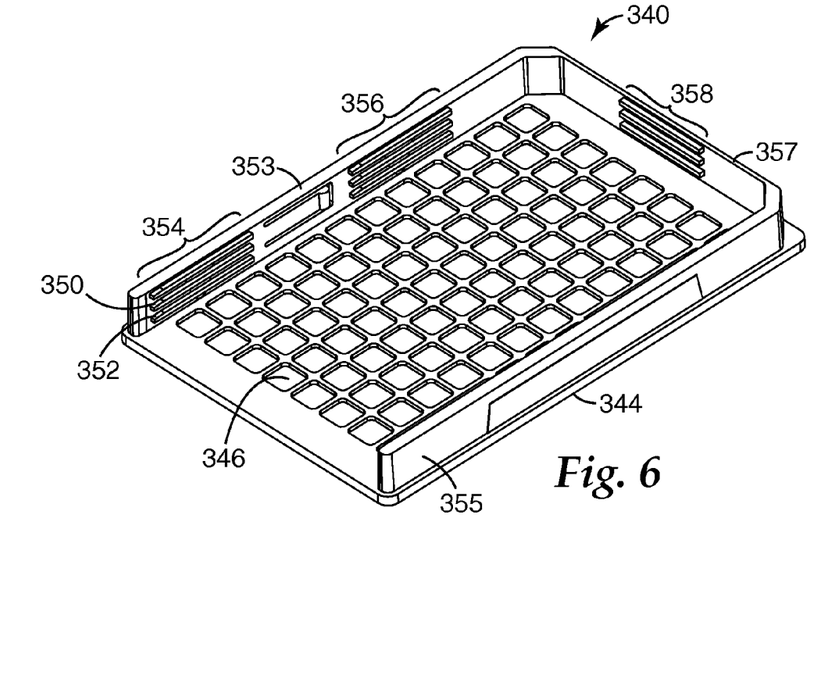
FIG. 6 is a perspective view of another exemplary embodiment of a positioning device according to the present invention.
Figure 7:
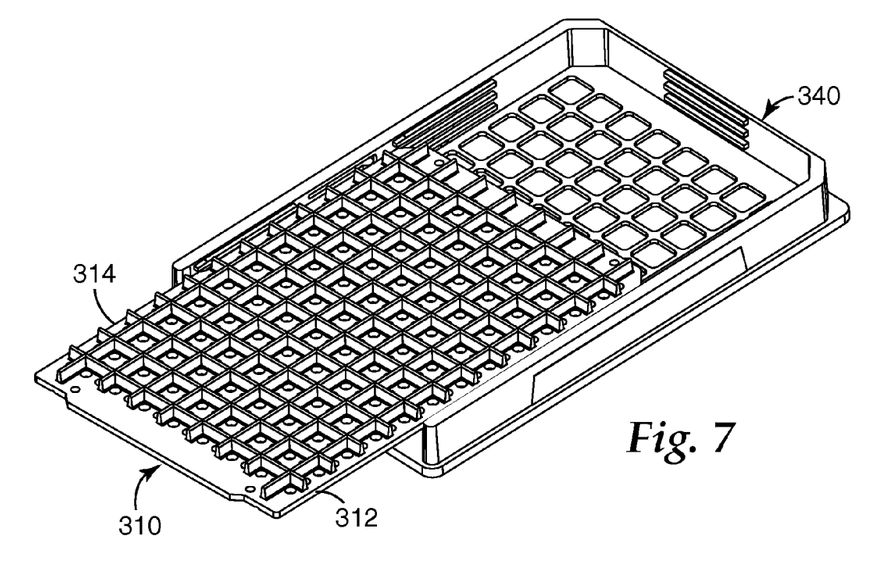
FIG. 7 is a perspective view of another exemplary embodiment of a sample processing device suspended within a positioning device according to the present invention.

FIGS. 6 & 7 depict an alternate embodiment of a positioning device 340 in which a sample processing device 310 is suspended within the positioning device to locate the process chambers of the sample processing device 310 within the focal plane of the sample compartment of an microplate reader. The sample processing device 310 may be located within the positioning device 340 by any suitable technique. It may be preferred that the sample processing device 310 be located within the positioning device 340 by sliding the sample processing device 310 into the positioning device 340. The sliding may preferably be performed by moving the sample processing device 310 in a direction generally parallel to its first major surface. Other techniques of loading sample processing devices into the positioning devices may also be used, e.g., snapping the sample processing device 310 into the channels in the positioning device 340, etc.

The sample processing device 310 may preferably include edges 312 and 314. The edges 312 and 314 may preferably be straight edges that are preferably parallel to each other as depicted in FIG. 7. It should be understood, however, that the edges of the sample processing device 310 may not be straight or parallel.

The positioning device 340 may preferably include channels used to suspend the sample processing device 310 along two or more edges of the sample processing device 310. The edges of the sample processing device 310 are preferably received within channels or other structures within the positioning device 34 such that the sample processing device 310 is suspended at a selected distance from the base 344 of the positioning device 340.

One embodiment of channels that may be used in connection with the positioning device 340 are depicted in FIGS. 6 & 7. The sample processing device 340 includes channels at two positions 350 and 352 located at different distances above the base 344 of the positioning device 340. The channels in the depicted embodiment are located in groups on opposing side walls 353 and 355 of the positioning device 340. Because of the perspective views, however, only groups 354 and 356 are seen on side 353. Corresponding channels are preferably located on the inside surface of side wall 355, but are hidden in the views of FIGS. 6 & 7.

The positioning device 340 also includes channels located in group 358 in the end wall 357 of the positioning device 340. As a result, a sample processing device 310 suspended within the positioning device 340 may be supported along three edges by the channels in the side walls 353 and 355 and end wall 357.

Although the positioning device 340 includes two positions at which a sample processing device 310 may be suspended, other positioning devices according to the present invention may provide only one position at which a sample processing device may be suspended. Still other positioning devices according to the present invention may provide three or more positions at which a sample processing device may be suspended.

The base 344 of the positioning device 340 may preferably include voids 346 that may be similar to voids 46 discussed above in connection with positioning device 40. If voids 346 are provided and are aligned with the process chambers to be read on the sample processing device 340, then sample processing device can be suspended within positioning device 340 in either direction. In other words, the process chambers may face the base 344 or away from the base 344. Furthermore, the base 344 may be placed on the floor of a sample compartment or the positioning device 340 may be loaded into the sample compartment with the base 344 supported above the floor of the sample compartment by the side walls 353 and 355 along with end wall 357.

It may be preferred that the edges of the sample processing device 310 fit tightly within the channels to retain the sample processing device 310 within positioning device 340 by friction. Many other alternative techniques may be used to retain sample processing device 310 within positioning device 340 such as clamps, adhesives, snap-fit structures, etc.

Although channels are used to suspend sample processing device 310 in the embodiment of FIGS. 6 & 7, it should be understood that many other structures could be used in place of channels, e.g., posts, rails, a frame, etc.

Figure 8:
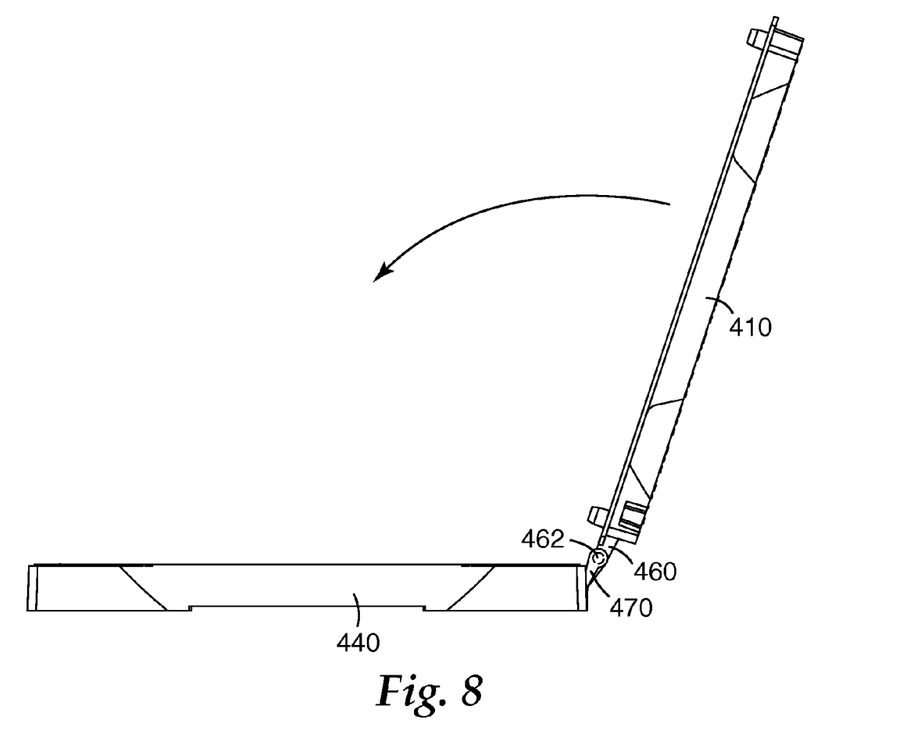
FIG. 8 is a side elevational view of a sample processing device and positioning device that are hinged together.
Figure 9:
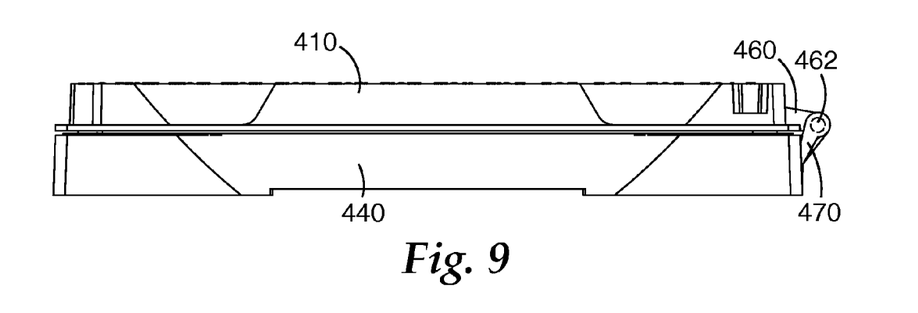
FIG. 9 is a side elevational view of the sample processing device and positioning device of FIG. 8 in which the sample processing device and positioning device are rotated together about the hinged connection.
Figure 10:
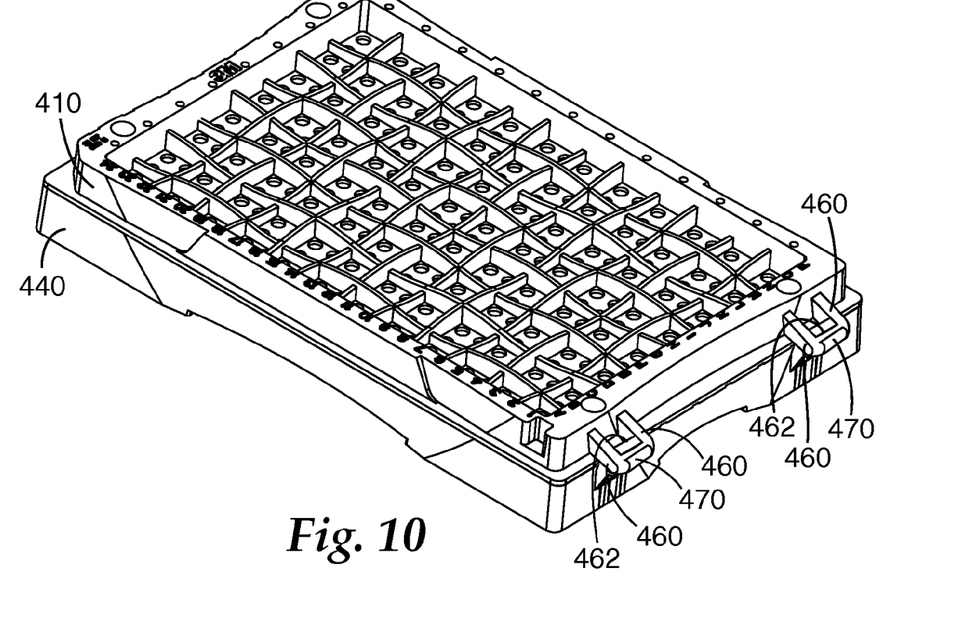
FIG. 10 is a perspective view of the sample processing device and positioning device of FIG. 9.

FIGS. 8-10 depict another exemplary embodiment of a sample processing device 410 and positioning device 440 that are rotationally connected to each other by one or more hinges. The rotational connection is preferably obtained by providing a first hinge structure on the sample processing device 410 and complementary hinge structure on the positioning device 440.

The depicted hinges include two pairs of hinge arms 460, with each pair of hinge arms 460 supporting a hinge pin 462 on the sample processing device 410. The positioning device 440 includes a pair of hinge pin retainers 470, each of which is adapted to receive a hinge pin 462 and retain it in a manner that allows for rotation of the sample processing device 410 and the positioning device 440 relative to each other about an axis defined by the hinge pins 462. The connection between the hinge pins 462 and the retainers 470 may be, e.g., a snap fit connection as is known in the art.

The hinges depicted in the embodiment of FIGS. 8-10 are only one embodiment of the many different hinges that could be used in connection with the present invention. Any other hinge or hinges may be used that provide for the desired rotational connection between the sample processing device 410 and the positioning device 440. It may be preferred, for example, that a living hinge be provided between the sample processing device 410 and positioning device 440 if the two components are molded together. In other alternatives, the hinge pin retainer may capture the hinge pin in a manner that requires destruction of at least a portion of the hinge to release the hinge pin (as opposed to the structures depicted in FIGS. 8-10 in which the hinge pins 462 may be snapped out of the retainers 470).

In other variations, the sample processing device 410 and positioning device 440 may be hinged along any suitable side of the components. In the depicted rectangular embodiment, the hinged connection is one of the short sides of the rectangle, although the components could be hinged along one of the long sides if so desired.

Figure 11:
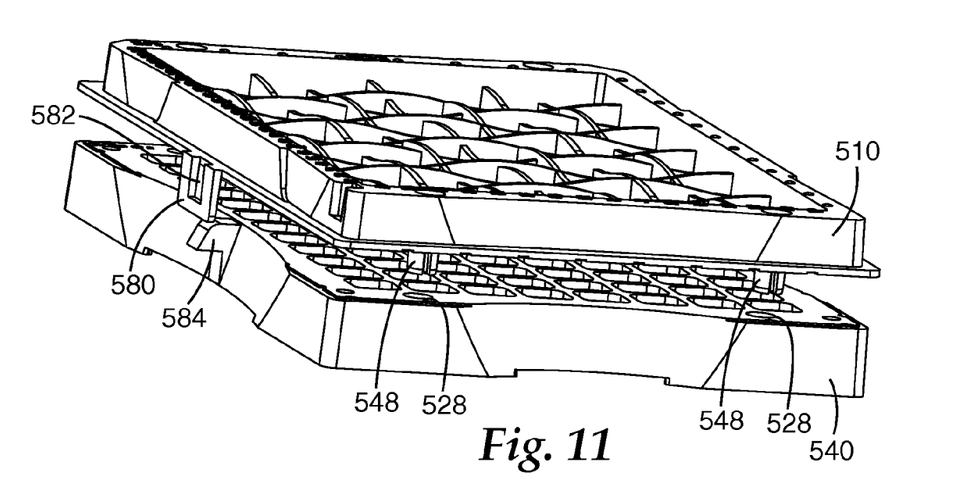
FIG. 11 is an exploded perspective view of another sample processing device and positioning device connected by locking tabs.

FIG. 11 depicts another embodiment of a sample processing device 510 and a positioning device 540 in which the sample processing device 510 includes retaining assembly in the form of a locking tab 580 with an opening 582 that receives a post 584 on the positioning device 540. The locking tab 580 and post 584 preferably retain the sample processing device 510 and the positioning device 540 connected when in use. The locking tab 580 can, however, be bent or deflected to release the two components for separation. Although not seen in the view of FIG. 11, it will typically be preferred that at least one other retaining assembly be provided on the opposite side of the sample processing device 510 and positioning device 540. The sample processing device 510 also includes posts 548 extending from the sample processing device 510 and openings 528 in the positioning device 540.

Figure 12:
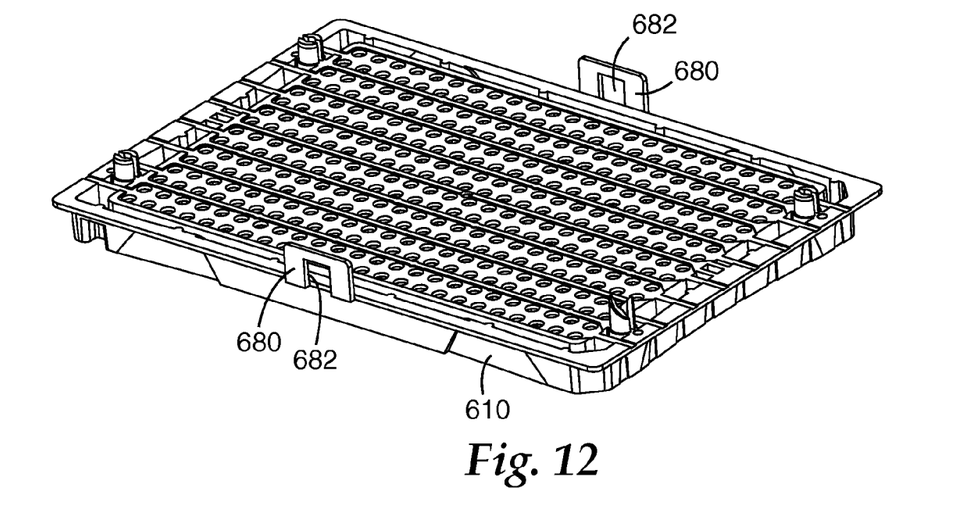
FIG. 12 is a perspective view of an sample processing device with a set of locking tabs in a different location than that depicted in FIG. 11.

FIG. 12 depicts another embodiment of a sample processing device 610 that includes locking tabs 610 on the long sides of a rectangular sample processing device 610 (as opposed to the short sides as seen in the sample processing device 510 of FIG. 11. The locking tabs 680 also include openings 682 adapted to receive a structure (e.g., post, etc.) on a complementary positioning device (not shown).

Figure 13:
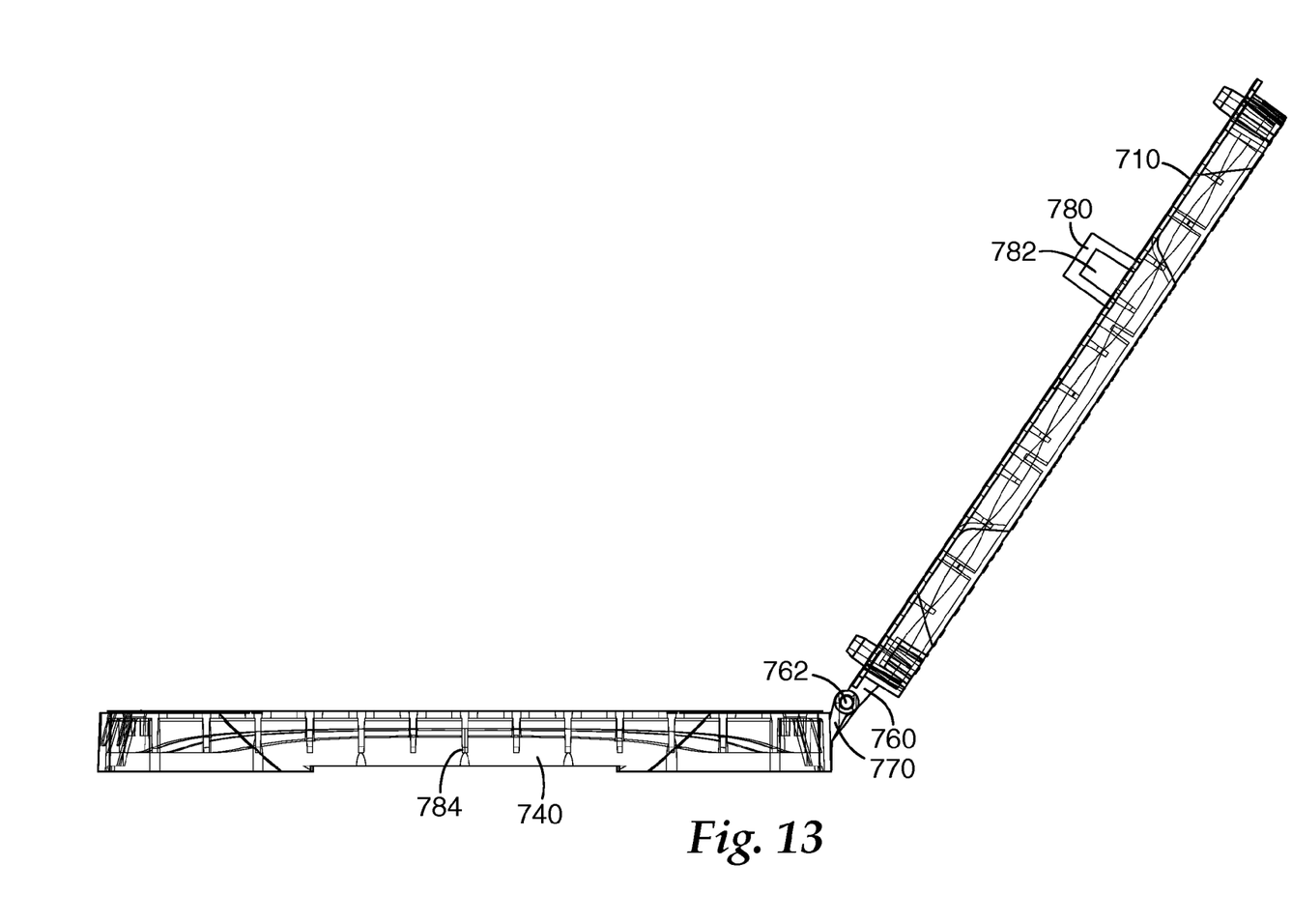
FIG. 13 is a side elevational view of a hinged sample processing device and positioning device in which the sample processing device includes locking tabs.

FIG. 13 depicts yet another embodiment of the invention in which a sample processing device 710 and positioning device 740 are attached together with a hinged connection and locking tabs. As seen in FIG. 13, the sample processing device 710 includes hinge arms 760 and a hinge pin 762 that is retained within a hinge pin retainer 770 on the positioning device 740. The sample processing device 710 also includes a locking tab 780 with an opening 782 adapted to receive a post 784 on the positioning device 740. The hinge structure and locking tab/post operate together in the depicted embodiment to retain the sample processing device 710 and the positioning device 740 together.

Methods of positioning a sample processing device within a microplate reader having a sample compartment with a floor and a focal plane spaced from the floor of the sample compartment may include locating a positioning device proximate the first major surface of a sample processing device. The sample processing device and the positioning device may then be located in the sample compartment of the microplate reader. It will typically be preferred that the positioning device be located between the first major surface of the sample processing device and the floor of the sample compartment.

It will typically be preferred that the process chambers in the sample processing device are located within the focal plane of the sample compartment when the sample processing device and the positioning device are located within the sample compartment. If the microplate reader is a top-reading system, it may be preferred that the positioning device be located between the first major surface of the sample processing device and the floor of the sample compartment to place the process chambers in the focal plane.

Methods of the present invention may also include determining the position of a focal plane within the sample compartment and selecting a positioning device that positions the process chambers of the sample processing device within the focal plane within the sample compartment. As discussed herein, a user may be provided with different positioning devices having different thicknesses, one or more shims along with a positioning device to adjust the thickness of the positioning device, or (in the case of suspension positioning devices), the positioning devices may provide two or more positions that effectively place a sample processing device at different heights above the floor of the sample compartment. Determination of the actual position of the focal plane within a given microplate reader may be accomplished empirically, based on manufacturer specifications, etc.

Methods of the present invention may also include registering or aligning the sample processing device on the positioning device. The alignment may be performed using alignment features on the positioning device that mate with complementary alignment features on the sample processing device. Alternatively, the alignment may be performed visually, with the sample processing device being held in a selected position on the positioning device by clamps, adhesives, magnetically, etc.

In addition to aligning the sample processing device on the positioning device, the methods of the present invention may also include aligning the positioning device within the sample compartment. For example, the positioning device may include alignment features that mate with complementary alignment features on the floor of the sample compartment. In yet another alternative, alignment of the sample processing device within the sample compartment may be accomplished by aligning the sample processing device itself within the compartment with only rough alignment of the sample processing device on the positioning device being required.

In the methods of the present invention, it may be preferred that the sample processing device is not fixedly attached to the positioning device. By "fixedly" we mean that the sample processing device, if attached to the positioning device, cannot be removed from the positioning device without destroying of the integrity of the fluidic features in the sample processing device such as the process chambers and main conduit. As such, even a rotationally connected sample processing device and positioning device are not "fixedly" attached to each other when the two components can rotate relative to each other about one or more hinges without destroying the integrity of the fluidic features.

By not fixedly attaching the sample processing device and positioning device together, the sample processing device and the positioning device can be temporarily separated as necessary for upstream processing steps. For example, if the sample processing devices are similar to those described in U.S. Pat. No. 6,627,159 B1 (Bedingham et al.) and U.S. Patent Application Publication Nos. U.S. 2002/0048533 A1 (Harms et al.) and U.S. 2002/0064885 (Bedingham et al.), a user may need to have access to the first major surface of the sample processing device (i.e., the surface placed on the positioning device) to complete the loading and processing of sample materials before locating the sample processing device on the positioning device for reading in an microplate reader. Alternatively, the sample processing device and the positioning device can be supplied in the form of a kit. In such a case, it is required to join the devices into an assembly prior to optical interrogation.

As used herein and in the appended claims, the singular forms "a," "and," and "the" include plural referents unless the context clearly dictates otherwise. Thus, for example, reference to "a process array" includes a plurality of process arrays and equivalents thereof known to those skilled in the art. Similarly, where two components or features are recited, it should be understood that more than two components or features are also included unless the context clearly dictates otherwise (e.g., "two channels" includes three or more channels).

All references and publications identified herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein.

Accordingly, the invention is to be limited only by the claims provided below and equivalents thereof.

The invention claimed is:

1. A method of positioning a sample processing device within a microplate reader having a sample compartment with a floor and a focal plane spaced from the floor of the sample compartment, the method comprising:

providing a sample processing device comprising at least one process array, wherein the at least one process array comprises a main conduit and a plurality of process chambers located along the main conduit, and wherein the sample processing device comprises a first major surface with edges at a periphery of the first major surface, and a carrier attached to the top of the major surface of the sample processing device, wherein the carrier comprises compression structures configured to transfer compressive forces to the sample processing device;

locating a positioning device proximate the first major surface of the sample processing device, wherein the positioning device comprises a z-axis thickness and a support surface;

retaining the sample processing device proximate the support surface of the positioning device, wherein the carrier provides sufficient force to flatten the sample processing device; and locating the sample processing device and the positioning device in the sample compartment of the microplate reader, wherein the positioning device is in contact with the floor of the sample compartment and located between the first major surface of the sample processing device and the floor, wherein the plurality of process chambers are spaced from the floor of the sample compartment by at least a height corresponding to the z-axis thickness, wherein the plurality of process chambers are located within the focal plane of the sample compartment, and wherein the plurality of process chambers would neither be located within the focal plane of the sample compartment nor spaced from the floor of the sample compartment without the positioning device located between the first major surface of the sample processing device and the floor of the sample compartment.

2. A method according to claim 1, wherein the support surface is substantially coextensive with an area of the first major surface occupied by the plurality of process chambers of the at least one process array, and wherein the support surface is located between the floor and the sample processing device.

3. A method according to claim 2, wherein the support surface comprises voids formed therein, wherein the first major surface of the sample processing device is visible through the positioning device.

4. A method according to claim 1, further comprising determining a position of a focal plane within the sample compartment and selecting a positioning device that positions the plurality of process chambers of the at least one process array within the focal plane within the sample compartment when the sample processing device and the positioning device are located within the sample compartment and the positioning device is located between the first major surface of the sample processing device and the floor of the sample compartment.

5. A method according to claim 1, further comprising registering the sample processing device on a support surface of the positioning device.

6. A method according to claim 1, wherein the positioning device comprises alignment features that mate with complementary alignment features on the sample processing device.

7. A method according to claim 6, wherein the alignment features of the positioning device comprise posts protruding from a support surface of the positioning device and wherein the complementary alignment features of the sample processing device comprise openings sized to receive the posts protruding from the support surface of the positioning device.

8. A method according to claim 6, wherein the alignment features of the positioning device comprise openings in the support surface of the positioning device, and wherein the complementary alignment features of the sample processing device comprise posts protruding from the first major surface of the sample processing device, wherein the openings in the positioning device are sized to receive the posts protruding from the first major surface of the sample processing device.

9. A method according to claim 1, wherein the retaining comprises clamping the positioning device and the sample processing device together.

10. A method according to claim 1, wherein the retaining comprises adhering the positioning device and the sample processing device together.

11. A method according to claim 1, wherein the retaining comprises capturing a post in a locking tab.

12. A method according to claim 1, wherein the sample processing device is not fixedly attached to the positioning device when the sample processing device and the positioning device are located within the sample compartment and the positioning device is located between the first major surface of the sample processing device and the floor of the sample compartment.

13. A method according to claim 1, wherein the sample processing device and the positioning device are rotationally connected to each other by one or more hinges.

14. The method according to claim 1, wherein the sample processing device is a microfluidic device.

15. The method according to claim 1, wherein the positioning device further comprises a base surface opposite the support surface, said base substantially coextensive with the support surface and resting on the floor when the positioning device is located in the sample compartment.

* * * * *